United States Patent
Mizobuchi et al.

(10) Patent No.: US 9,879,223 B2
(45) Date of Patent: Jan. 30, 2018

(54) METHODS AND SYSTEMS FOR THE REDUCTION OF LEUKOCYTES IN A BIOLOGICAL FLUID

(71) Applicant: FENWAL, INC., Lake Zurich, IL (US)

(72) Inventors: Yoshikazu Mizobuchi, Mundelein, IL (US); JoAnne B. Alfaro, Arlington Heights, IL (US)

(73) Assignee: Fenwal, Inc., Lake Zurich, IL (US)

( * ) Notice: Subject to any disclaimer, the term of this patent is extended or adjusted under 35 U.S.C. 154(b) by 165 days.

(21) Appl. No.: 14/446,418

(22) Filed: Jul. 30, 2014

(65) Prior Publication Data

US 2016/0032246 A1 Feb. 4, 2016

(51) Int. Cl.
  *C12N 5/00* (2006.01)
  *C12N 5/07* (2010.01)
  *C12N 5/0787* (2010.01)

(52) U.S. Cl.
  CPC ......... *C12N 5/0642* (2013.01); *C12N 5/0087* (2013.01)

(58) Field of Classification Search
  CPC .. C12N 5/0642; C12N 5/0635; C12N 5/0636; A61M 1/362; A61M 1/36
  See application file for complete search history.

(56) References Cited

U.S. PATENT DOCUMENTS

| | | | |
|---|---|---|---|
| 5,143,982 A * | 9/1992 | Niino | 525/400 |
| 5,223,398 A | 6/1993 | Kortright et al. | |
| 5,407,581 A * | 4/1995 | Onodera et al. | 210/654 |
| 6,221,315 B1 * | 4/2001 | Giesler | C12Q 1/24 210/222 |
| 7,057,007 B2 * | 6/2006 | Nakamoto et al. | 528/308.6 |
| 7,173,124 B2 | 2/2007 | Deggerdal et al. | |
| 7,541,184 B2 | 6/2009 | Berenson et al. | |
| 7,985,340 B2 | 7/2011 | Almaasbak et al. | |
| 2011/0306070 A1 | 12/2011 | Campbell et al. | |
| 2014/0263070 A1 | 9/2014 | Mizobuchi et al. | |

OTHER PUBLICATIONS

Polyethylene, oxidized. Datasheet [online]. Sigma-Aldrich, 2017 [retrieved on Aug. 9, 2017]. Retrieved from the Internet: <URL: http://www.sigmaaldrich.com/catalog/product/aldrich/191914?lang=en&region=US>.*
Product literature entitled M-Beads Magnetic Silica Beads Tools dated 2010 from MoBiTec GmbH.
Product literature entitled M-Beads Magnetic Silica Beads DNA Allround dated 2012 from MoBiTec GmbH.
Product literature entitled M-Beads Magnetic Silica Beads DNA dated 2012 from MoBiTec GmbH.

* cited by examiner

*Primary Examiner* — Kara Johnson
(74) *Attorney, Agent, or Firm* — Cook Alex Ltd.

(57) ABSTRACT

Methods and systems for removing leukocytes from a biological fluid are disclosed. The methods and systems include a chamber containing particles to which the leukocytes adhere. Such particles may carry an electrostatic charge. In one example, the particles comprise a polymer having an acid number of 5 or greater.

16 Claims, 2 Drawing Sheets

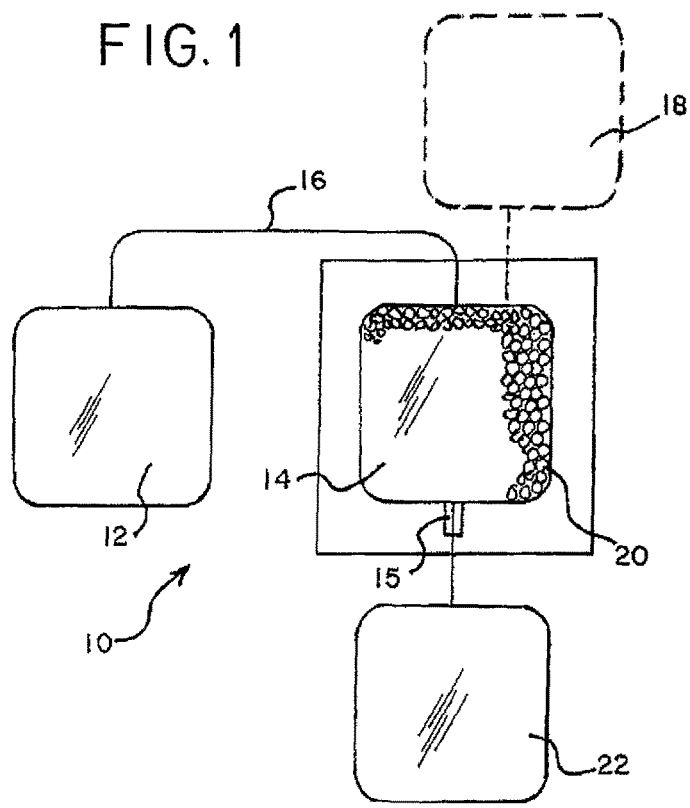

FIG. 2

| Particles | Chemical Property | | Physical Property |
|---|---|---|---|
| | Material Information | Acid # | Drop Point / °C |
| AC395A | Oxidized Polyethylene Homopolymer | 41 | 137 |
| AC316A | Oxidized Polyethylene Homopolymer | 16 | 140 |
| AC307 | Oxidized Polyethylene Homopolymer | 7 | 140 |

FIG. 3

| Description | | Powder/grams | Sample ID | WBC | Neutrophil | Lymphocyte | Platelet |
|---|---|---|---|---|---|---|---|
| Pre-Filtration | | N/A | N/A | 4.3 | 2.3 | 1.7 | 259 |
| Post-Filtration | Run 1 | 1.04 | 677-9 | 0.2 | N/D | N/D | 5 |
| | Run 2 | 1.07 | 677-10 | 0.3 | N/D | N/D | 2 |

FIG. 4

| Description | | | Powder/grams | Sample ID | WBC | Neutrophil | Lymphocyte | Platelet |
|---|---|---|---|---|---|---|---|---|
| Pre-Filtration | | | N/A | N/A | 4.1 | 2.4 | 1.3 | 196 |
| Post-Filtration | AC395A | Run 1 | 1.06 | 679-395-1 | 0.5 | N/D | N/D | N/D |
| | | Run 2 | 1.07 | 679-395-2 | 0.4 | N/D | N/D | N/D |
| | AC316A | Run 1 | 1.05 | 679-316-1 | 0.9 | N/D | N/D | N/D |
| | | Run 2 | 1.06 | 679-316-2 | 1 | N/D | N/D | N/D |
| | AC307 | Run 1 | 1.04 | 679-307-1 | 2.3 | 1.3 | 0.9 | 13 |
| | | Run 2 | 1.1 | 679-307-2 | 2.3 | 1.4 | 0.8 | 12 |

FIG. 5

| Description | | | Powder/grams | Sample ID | WBC | Neutrophil | Lymphocyte | Platelet |
|---|---|---|---|---|---|---|---|---|
| Pre-Filtration | | | N/A | N/A | 5.1 | 2.7 | 1.9 | 231 |
| Post-Filtration | AC395A | Run 1 | 1.04 | 677-24-1 | 0.3 | N/D | N/D | 2 |
| | | Run 2 | 1.07 | 677-24-2 | 0.3 | N/D | N/D | 5 |
| | | Run 3 | 1.08 | 677-24-395-1 | 0.2 | N/D | N/D | 1 |
| | | Run 4 | 1.06 | 677-24-395-2 | 0.3 | N/D | N/D | 3 |
| | AC316A | Run 1 | 1.06 | 677-24-316-1 | 1.5 | 0.4 | 0.9 | 19 |
| | | Run 2 | 1.13 | 677-24-316-2 | 0.7 | N/D | N/D | 6 |
| | | Run 3 | 1.05 | 677-24-316-3 | 1.7 | 0.6 | 0.8 | 33 |
| | AC307 | Run 1 | 1.1 | 677-24-307-1 | 4.6 | 2.1 | 2 | 90 |
| | | Run 2 | 1.1 | 677-24-307-1 | 4.5 | 2.1 | 1.9 | 75 |

METHODS AND SYSTEMS FOR THE REDUCTION OF LEUKOCYTES IN A BIOLOGICAL FLUID

FIELD OF THE DISCLOSURE

The present disclosure is directed to methods and systems for reducing the amount of leukocytes in a biological fluid, such as blood or blood components.

BACKGROUND

Before transfusing blood or a collected blood component to a recipient in need of the component, it is often desirable to minimize the presence of matter, including certain cells or other materials, that may cause undesired side effects in the recipient. For example, because of the potential of possible adverse reactions in the recipient, it is generally considered desirable to reduce the number of leukocytes in blood components before transfusion. Reduction in the concentration of leukocytes is often referred to as "leukoreduction" or "leukodepletion."

Filters used to accomplish leukoreduction in blood products today commonly employ a filter media comprising melt-blown spun polyester fibers disposed between mating walls of a filter housing, with inlet and outlet ports associated with the housing providing flow to and from the interior of the filter. While filters are widely accepted in the field of blood collection and processing, and have generally worked satisfactorily, they are not without certain drawbacks. For example, filter performance may vary, contributing to inconsistencies in the effectiveness of the leukocyte removal. Filters may also result in the removal of other materials and/or can be expensive.

Thus, there continues to be a desire for additional leukoreduction devices and/or methods. For example, it would be desirable to provide a system and method that allows for more predictability in the effectiveness of the leukoreduction of a blood product, and provides for lot-to-lot repeatability of the leukoreduction process.

SUMMARY

In one general aspect, the present disclosure is directed to a method for removing leukocytes from a biological fluid. The method includes introducing a quantity of a biological fluid including leukocytes and other components into a biocompatible chamber containing particles to which the leukocytes are attracted. The biological fluid is contacted, directly or indirectly, inside said chamber by the particles so as to attract and adhere leukocytes in the biological fluid thereto. The other remaining components may then be removed from the chamber by, e.g., fluid pressure.

In another general aspect, the present disclosure is directed to a system for reducing the number of leukocytes in a biological fluid. The system includes a container having an interior chamber containing particles to which the leukocytes are attracted. The system may further include a flow path in openable fluid communication with the chamber so as to permit the flow of biological fluid therethrough.

In a more specific aspect, the particles may comprise a polymer, and more specifically a homopolymer, such as an oxidized polyethylene homopolymer, such as but not exclusively in powder form.

These and other more particular aspects of the present subject matter are set forth in the following description and accompanying drawings.

BRIEF DESCRIPTION OF THE DRAWINGS

FIG. 1 is a schematic view of a system in accordance with the present disclosure;

FIG. 2 is a table identifying the chemical and physical properties of three different negatively chargeable particles that may be used in the method and system of the present disclosure;

FIG. 3 is a table showing the leukocyte reduction from fresh whole blood using one of the three particle types identified in the table of FIG. 2;

FIG. 4 is a table showing the leukocyte reduction from fresh whole blood using each of the three particle types identified in the table of FIG. 2; and FIG. 5 is a table showing the leukocyte reduction from whole blood that has been held at room temperature for 24 hours using each of the three particle types identified in the table of FIG. 2.

DETAILED DESCRIPTION OF THE EMBODIMENTS

The present disclosure is directed to systems and methods for reducing the quantity of leukocytes in a biological fluid. As shown in FIG. 1, the system 10 may include or be connectable to a source of biological fluid 12 and a chamber 14 where the biological fluid is combined and contacted with particles 20 that attract, adhere to or retain leukocytes to effect the reduction and removal of leukocytes from the biological fluid. The mechanism of such attraction is believed to be associated with an electric charge, such as an ionic or electrostatic charge. Additionally and/or alternatively, the degree of attraction is believed to be associated with and/or to vary with the acid number of the particle, as explained in more detail later. To these ends, the particles 20 may be electrically chargeable, and carry an ionic or electrostatic charge, such as a negative charge, and/or the particles 20 may have an acid number sufficient to aid attraction, such as, e.g., from about 5 to about 50 or higher.

The source 12 may be in flow communication with the chamber 14 by means of a tubing 16, which defines an openable flow path between container 12 and chamber 14, with flow control devices such as, for example, pumps, clamps, internal frangible closures, injection sites, or the like, as are desired. The particles 20 are preferably introduced into the chamber 14 at the time of manufacture. Alternatively, the particles 20 may be separately introduced into chamber 14 before, during or after introduction of the biological fluid into chamber 14, from a source 18 where such particles may, for example, be in a suspension comprising, e.g., saline. System 10 may also optionally include a collection container 22 for collecting the unbound (i.e. leukocyte-depleted) components from chamber 14, if desired.

In accordance with one aspect of the present disclosure, the source of biological fluid 12 may be a blood donor. In another preferred embodiment, the source 12 may be a container of biological fluid that has been previously collected from a donor.

The biological fluid may be any biological fluid that includes leukocytes. In one example, the biological fluid may be whole blood. In another example, the biological fluid may be a component of blood. Where the source of biological fluid 12 is previously collected blood, the blood may contain other material, such as anticoagulant, and still be regarded as whole blood. Container 12 that holds the biological fluid may be made of a medical-grade polymeric material such as, but not limited to, plasticized polyvinyl chloride, or any other suitable material.

Chamber 14 (which may also be referred to as a mixing chamber, processing chamber, holding chamber, or the like) may be any receptacle that is suitable for receiving blood, components of blood, or any other biological fluid. In one embodiment, mixing chamber 14 may be a sealed container made of a polymeric material.

In accordance with the present disclosure, the particles 20 may comprise a polymer, and more particularly an oxidized polymer, such as an oxidized polyethylene homopolymer. Non-limiting examples of such particles include DuPont™ Hytrel® 3078 thermoplastic polyester elastomer, available in pellet form, and the Honeywell A-C® high density oxidized polyethylene homopolymers designated A-C 307, A-C 316A and A-C 395A, in powder form. The particle size of the powder forms of the homopolymer are selectable or controllable, resulting in a more highly repeatable degree of leukoreduction. A negative electrostatic and/or ionic charge induced on the surface of the particles, is understood to provide a strong attraction to leukocytes. It is contemplated that the particles 20 will be retained within the chamber 14 by means of, e.g., a mesh lining having a pore size smaller than the size of the particles, while still large enough to permit the desired cellular material to pass therethrough.

The particles 20 have an acid number indicative of the hydrophilic nature of the particles and which correlates with the degree of attraction to leukocytes. As explained later, in certain studies that were run using of the above-identified homopolymers, the use of homopolymers with higher acid numbers resulted in greater leukoreduction. It is presently contemplated that particles with acid numbers between about 5 and about 50 or higher, such as between about 7 and about 41, may be useful in leukocyte reduction.

In accordance with the method of reducing leukocytes in a biological fluid as disclosed herein, a quantity of a biological fluid such as whole blood or a blood component that has been separated from whole blood that includes leukocytes and other components is introduced from a source 12 such as a container or directly from a patient into biocompatible chamber 14. The biological fluid contacts the particles 20 contained within the chamber 14. The particles 20 exhibit an affinity for the leukocytes, attracting and retaining them within the chamber 14. Alternatively, chamber 14 may be provided with particles 20 from source 18. The biological fluid remains in contact with particles 20 in the chamber 14 for a selected period time.

The other remaining components which have now had their leukocyte content reduced may then be removed from the chamber, by for example flowing the remainder of the biological fluid out port 15 of chamber 14 into a collection container 22. The collected, leukoreduced biological fluid may be stored and/or transfused to a recipient or patient. The collected leukocytes may be disposed of, or may be further processed to release them from the particles 20 for subsequent uses or applications.

In a non-limiting example, a chamber comprising as plastic cylindrical tube with a diameter of 10 mm was packed to a depth of 22 mm with the oxidized polymer particles having a packed density of 0.58 grams/cm$^3$. The dead volume in the packed column was 0.611 mL. The particles were retained in the tube by a mesh disposed on the flat bottom of the tube. Blood was fed to the tube at a rate of 1 mL/10 min, and the estimated maximum residence time in the packed column was 3.1 minutes. These conditions will vary depending on the packed condition of the particles, as well as the configuration of the chamber.

Leukoreduction in accordance with the methods and systems disclosed herein allow the leukoreduction to be tailored to specific needs or targets such as the percentage of the leukocytes to be reduced. These specific needs and targets may be achieved by selecting specific homopolymers, or by combining two or more homopolymers in combination within the chamber 14, such as mixed together or arranged separately for sequential contact with the blood or blood components, to achieve a desired separation.

Study

A study was performed in which three different oxidized polyethylene homopolymer powders available from Honeywell (A-C 307, A-C 316A and A-C 395A) were used in the system and method described above. With reference to FIG. 2, certain of the chemical and physical properties of the three materials are set forth, one of which is the acid number. The acid number is specified by the manufacturer and is indicated as being determined in accordance with ASTM D-1386. Each of the three homopolymers has a different acid number, ranging from a low of 7 (for A-C 307) to a high of 41(for A-C 395A). Based on the testing, it has been determined that the higher the acid number, the greater the ability to attract leukocytes.

The test method comprised packing the homopolymer powders in 5 mL polypropylene pipet tips. This was accomplished by first suspending the powders in saline. It is believed that suspension of the particles in saline "primes" the particles so that the oxidized particles become ionized. After packing the pipets with powder was completed, an attachment connected to a pump to feed blood was placed on top of the pipet tip. Blood was then fed at a rate of 10 mL/hr, the saline being forced out of the pipet before the blood reached the packed particles. In each run, 3 mL of whole blood plus anticoagulant (CPD) was used, with a saline prime before filtration, at the controlled flow rate of 10 mL/hr and with a total filtration or passage time of 12 minutes. The blood passing through the packed particles was collected, and blood cell count analyses were performed using a Sysmex KX-21 N hematology analyzer.

FIGS. 3, 4 and 5 present data relative to the pre-filtration and post filtration whole blood, providing blood cell counts for leukocytes or white blood cells (WBC), Neutrophils, Lymphocytes. Neutrophils and lymphocytes are the main components in leukocytes (or in general term white blood cells). The value for WBC is total cell counts for leukocytes, and the values for neutrophils and lymphocytes are part of WBC cell counts.] and Platelets, in units of $10^3/\mu L$. The table of FIG. 3 shows the result of a preliminary study on leukocyte elimination in fresh whole blood using A-C 395A homopolymer, the data showing a significant reduction of each of the four identified blood components, with remaining Neutrophils and Lymphocytes being non detectable ("N/D"), where indicated on the table. The table of FIG. 4 permits a comparison of efficacy of the three different homopolymers by acid number, again using fresh whole blood, and indicates that the higher the acid number, the more effective the homopolymer in removing the identified blood components. The table of FIG. 5 presents data from a study similar to that set forth in FIG. 4, except that the whole blood was maintained at room temperature for 24 hours prior to testing. However, the blood cell count analysis permits a conclusion similar to that of FIG. 4 in that the higher the acid number, the more effective the homopolymer in removing the identified blood components.

From the study, it can be appreciated that a desired degree of leukocyte removal may be obtained by selection of a particulate having an appropriate acid number, and that by blending particulates of different acid numbers, an effective acid number of the blend can be obtained.

Examples of Different Aspects

Without limiting any of the foregoing, the subject matter described herein may be found in one or more apparatus or methods. For example, in a first aspect of the disclosure a method for removing leukocytes from a biological fluid is provided that comprises introducing a quantity of a biological fluid including leukocytes and other components into a biocompatible chamber; contacting said biological fluid with one or more removal devices comprising particles inside said chamber that attract and adhere to leukocytes; and removing said other components from said chamber.

In a second aspect of the disclosed method, the particles are chargeable and may be negatively chargeable, and/or comprise a polymer, such as a homopolymer, more particularly a polyethylene homopolymer, and even more particularly an oxidized polyethylene homopolymer.

In a third independent aspect of the method, the particles have an acid number of about 5 or greater, such as 7 or greater, or between about 5 and 50 such as between about 7 and 41.

In a fourth independent aspect of the method, the particles carry an ionic or electrostatic charge, which may be a negative charge.

In a fifth aspect of the method, the biological fluid comprises blood component(s).

In a sixth aspect of the method, the blood comprises whole blood.

In another aspect of the disclosure, a system is provided for removing leukocytes from a biological fluid comprising a chamber containing particles that attract and adhere to leukocytes.

In a second aspect of the disclosed system, the particles comprise a polymer, in particular a homopolymer, more particularly a polyethylene homopolymer, and even more particularly an oxidized polyethylene homopolymer.

In a third aspect of the system, the particles have an acid number of about 5 or greater, such as 7 or greater, or between about 5 and 50 such as between about 7 and 41.

In a fourth aspect of the system, the particles carry an ionic or electrostatic charge, particularly a negative charge.

In a fifth aspect of the system, the particles comprise a blend or sequential contact arrangement of different homopolymers or other attractive particles.

In a sixth aspect of the system, the two or more different homopolymers other attractive particles may be selected to enhance the retention of leukocytes within the chamber.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims.

The invention claimed is:

1. A method for achieving a desired degree of leukocyte depletion in a biological fluid including leukocytes comprising:
   a) flowing a quantity of a first type of charged particle having a first acid number into a treatment chamber from a first container;
   b) flowing a quantity of a second type of charged particle having a second acid number, wherein the second type of charged particle is different from the first type of charged particle into the treatment chamber from a second container in an amount to achieve a blend of charged particles in the treatment chamber having an effective acid number to achieve the desired degree of leukocyte depletion;
   c) flowing a quantity of biological fluid from a source container into the treatment chamber at a flow rate to achieve a predetermined total filtration time; and
   d) after the total filtration time has elapsed, flowing leukocyte-depleted biological fluid from the treatment container to a collection container.

2. The method of claim 1 wherein the charged particles carry an ionic or electrostatic charge.

3. The method of claim 2 wherein said ionic or electrostatically-charged particles comprise a polymer.

4. The method of claim 2 wherein said ionic or electrostatically-charged particles comprise a homopolymer.

5. The method of claim 2 wherein said ionic or electrostatically-charged particles comprise a polyethylene homopolymer.

6. The method of claim 2 wherein said ionic or electrostatically-charged particles comprise an oxidized polyethylene homopolymer.

7. The method of claim 1 said biological fluid comprises blood.

8. The method of claim 7 wherein said blood comprises whole blood.

9. The method of claim 1 wherein the total filtration time is 12 minutes.

10. A system for removing leukocytes from a biological fluid containing leukocytes and other components, the system comprising:
    a) a treatment chamber;
    b) a first container containing a suspension of a first type of particles that carry an ionic or electrostatic charge, the first container connected to the treatment chamber by a first fluid flow path for introducing a quantity of the first type of particles into the treatment chamber;
    c) a second container containing a suspension of a second type of particles that carry an ionic or electrostatic charge wherein the second type of particles are different from the first type of particles, the second container connected to the treatment chamber by a second fluid flow path for introducing a quantity of the second type of particles into the treatment chamber;
    d) a source container containing the biological fluid connected to the treatment chamber by a third fluid flow path for introducing a quantity of the biological fluid into the treatment chamber; and
    e) a collection container connected to the treatment chamber by a fourth fluid flow path for receiving leukocyte-depleted biological fluid.

11. The system of claim 10 wherein said first type and second of particles comprise a polymer.

12. The system of claim 11 wherein said first type and second type of particles have an acid number of 5 or greater.

13. The system of claim 10 wherein said first type and second of particles comprise a homopolymer.

14. The system of claim 10 wherein said first type and second of particles comprise a polyethylene homopolymer.

15. The system of claim 10 wherein said first type and second of particles comprise an oxidized polyethylene homopolymer.

16. The system of claim 10 wherein the treatment chamber further comprises a mesh lining having a pore size for retaining the first type and second type of particles within the removal device, while permitting the leukocyte-depleted components to pass through.

* * * * *